United States Patent
Chang et al.

(10) Patent No.: US 7,362,428 B2
(45) Date of Patent: Apr. 22, 2008

(54) HIGHLY SENSITIVE DEFECT DETECTION METHOD

(75) Inventors: Chung-I Chang, Hsinchi (TW); Ferris Liu, Pingtung (TW)

(73) Assignee: Promos Technologies Inc., Hsinchu (TW)

(*) Notice: Subject to any disclaimer, the term of this patent is extended or adjusted under 35 U.S.C. 154(b) by 218 days.

(21) Appl. No.: 11/121,902

(22) Filed: May 5, 2005

(65) Prior Publication Data
US 2006/0187446 A1   Aug. 24, 2006

(30) Foreign Application Priority Data
Feb. 22, 2005 (TW) .............. 94105298 A

(51) Int. Cl.
*G01N 21/89* (2006.01)

(52) U.S. Cl. .................. 356/237.5; 356/237.4; 382/144; 382/145

(58) Field of Classification Search .. 356/237.4–237.5; 382/144–145
See application file for complete search history.

(56) References Cited
U.S. PATENT DOCUMENTS
5,432,607 A * 7/1995 Taubenblatt ............... 356/364
* cited by examiner

*Primary Examiner*—Layla G. Lauchman
*Assistant Examiner*—Rebecca C Slomski
(74) *Attorney, Agent, or Firm*—Rabin & Berdo, PC

(57) ABSTRACT

A highly sensitive defect detection method is disclosed. A medium with a refractive index greater than 1 is formed on a sample. As a result, incident light projected by a defect detecting system attenuates less when reaching the bottom defects. The detection sensitivity of the defect detecting system is enhanced accordingly.

10 Claims, 3 Drawing Sheets

HIGHLY SENSITIVE DEFECT DETECTION METHOD

RELATED APPLICATIONS

The present application is based on, and claims priority from, Taiwan Application Serial Number 94105298, filed Feb. 22, 2005, the disclosure of which is hereby incorporated by reference herein in its entirety.

BACKGROUND OF THE INVENTION

1. Field of Invention

The invention relates to a highly sensitive defect detection method and, in particular, to a method for detecting bottom defects of a device pattern in semiconductor wafers.

2. Related Art

Semiconductor processes employ complex steps such as deposition, etching, chemical mechanical polishing (CMP), to form devices (e.g. transistors, metal wires, and capacitors) with various kinds of shapes and patterns. However, there may be minute particles or residues left on the surface or bottom of the device pattern in these processes. Such residues or particles are considered as defects in the device pattern and may affect the performance and quality of semiconductor devices.

Therefore, the defect detection of semiconductor devices is an important step in the fabrication. A good defect detection method can find out small defects on the device pattern to ensure the semiconductor product quality and to provide process engineers with faithful data for adjustments.

The conventional defect detection method uses a defect detecting system to project an incident beam at a particular angle on the semiconductor wafer and scan through the whole wafer. When the beam hits a defect on the device pattern, the incident light is scattered. Several detectors are disposed around the device to receive the light reflected by the surface of the device pattern and scattered by the defect. Such a signal is compared with that from the neighboring regions of the same wafer, thereby determining the position and number of defects. For example, FIG. 1 shows a conventional defect detection method. An incident beam 104 is projected on the semiconductor wafer 100. If the device pattern 102 of the wafer 100 does not have any defect on its surface and bottom, a reflected beam 104' is obtained without any scattered light. If the device pattern 102 of the wafer 100 has a surface defect 110 and/or a bottom defect 110, these defects will scatter the incident beam 104 and produce scattering light 112. Since the incident light 104 is scattered by the defects 110, 108, the intensity of the reflected light 104' is weakened. Detectors 106 receive the reflected light 104' and scattered light 112. They further compare the signals with the intensity of the reflected light 104 and scattered light 112 from several neighboring device patterns of the same wafer to determine the defect distribution in the device pattern.

However, the defect 108 on the surface of the device pattern 102 can be directly hit by the incident light, whereas the bottom defect 110 receives less light due to the height and pitch of the pattern. As a result, the intensity of the light scattered from the bottom defect 110 is much weaker than that from the surface defect 108. Therefore, it is harder to detect the bottom defect 108 of the device pattern 102. If one increases the intensity of the incident light 104 for enhancing the intensity of the light scattered from the bottom defect 110 of the device pattern 102, the intensity of the light scattered from the surface defect 108 is also increased. Moreover, the noise intensity is enhanced also. Thus, the signal-to-noise (S/N) ratio is reduced. In the end, it is still very difficult to detect the bottom defects with high sensitivity. The detection result may be even worse than before.

On the other hand, there is a relation between the device resistance and its dimension:

$$R = \rho \times 1/(h \times w).$$

As the size of the semiconductor device pattern is further reduced while the coefficient of resistance $\rho$ and the length of the device pattern 1 remain the same, one has to increase the height h if the width w is to be reduced so that the resistance R is not increased. We take a metal wire as an example in FIG. 2. When the device pattern size on the wafer 100 shrinks from 0.2 μm in the left plot to 0.1 μm in the right plot, the line width of the metal wire 102 (i.e. the device pattern) changes from $w_1$ of 0.2 μm to $w_2$ of 0.1 μm. The pitch between two device patterns also changes from $d_1$ of 0.2 μm to $d_2$ of 0.1 μm. In this case, due to the narrow pitch, the incident light 104 projected to the pitch $d_2$ of the device pattern 102 is less than the pitch $d_1$. Moreover, using the same material (same coefficient of resistance) and the same length of device pattern, the height of the device pattern 102 increases from $h_1$ to $h_2$ if one wants to obtain the same resistance. Therefore, the aspect ratio h/d increases. As this factor increases, the number of reflections of the incident light 104 in $d_2$ also increases (as indicated by the arrow). However, the light intensity attenuates with the reflections. Therefore, the energy intensity of the incident light 104 reaching the bottom of the pitch $d_2$ is lower than that reaching the bottom of the pitch $d_1$. Accordingly, the intensity of scattering light from the bottom defect of the pitch $d_2$ is lower. It is thus not good for detecting the bottom defects in a device pattern.

Therefore, we need a defect detection method that is not only able to detect defects on the surface of a device pattern, but also sensitive to defects at the bottom of the device pattern.

SUMMARY OF THE INVENTION

It is an object of the invention to provide a highly sensitive defect detection method, particularly a method for detecting bottom defects on a device pattern of a sample.

In accord with the above object, a preferred embodiment of the invention forms a medium on a sample with several device patterns. A beam of light is projected by a defect detecting system on the medium-covered sample. The light penetrates through the medium and scans through the sample surface. At least one detector is used to receive the scattering light and reflected light from the sample to obtain the intensity of the reflected and scattering light of each point on the sample. Afterwards, the intensity of the reflected and scattering light from a few consecutive device patterns is compared with one another to determine the defects in them.

The sample is a substrate with semiconductor devices disposed on its surface. In particular, it is a semiconductor wafer having device patterns with a high aspect ratio. The medium coated on the sample can be a material with a refractive index greater than 1, transparent for incident light, and not affecting the sample. Such materials can be, for example, the dielectric material (e.g. silicon oxide) in a semiconductor process, the photo resist, or any liquid that does not erode, oxidize, or dissolve the sample (e.g. deionized water and mineral oils). The defect detecting system can be any existing optical defect detecting system.

An advantage of the invention is to increase the ability of a conventional defect detecting system to detect defects at the bottom of device patterns on a sample.

Another advantage of the invention is to solve the problem in the conventional defect detecting method which, when the device patterns get smaller, is unable to detect bottom defects of device patterns with high sensitivity because either the signals of bottom defects in a device pattern are weak or the signals of bottom defects are interfering with the signals of the surface defects or noises.

A further advantage of the invention is that the invention can be conveniently used in various kinds of conventional defect detecting systems without the need to make complicated modifications.

BRIEF DESCRIPTION OF THE DRAWINGS

These and other features, aspects and advantages of the invention will become apparent by reference to the following description and accompanying drawings which are given by way of illustration only, and thus are not limitative of the invention, and wherein.

DETAILED DESCRIPTION OF THE PREFERRED EMBODIMENT

The present invention will be apparent from the following detailed description, which proceeds with reference to the accompanying drawings, wherein the same references relate to the same elements.

The disclosed method forms a medium on a sample. A defect detecting system then detects defects on the sample. The defect detecting system projects a beam of light on the sample and scans through each point of the sample after the light penetrates through the medium. At least one detector of the defect detecting system is used to receive light scattered and reflected from each point on the sample. The intensity of the scattered and reflected light of all points is compared to find out at least one defect or a defect distribution on the sample.

Figure 1:
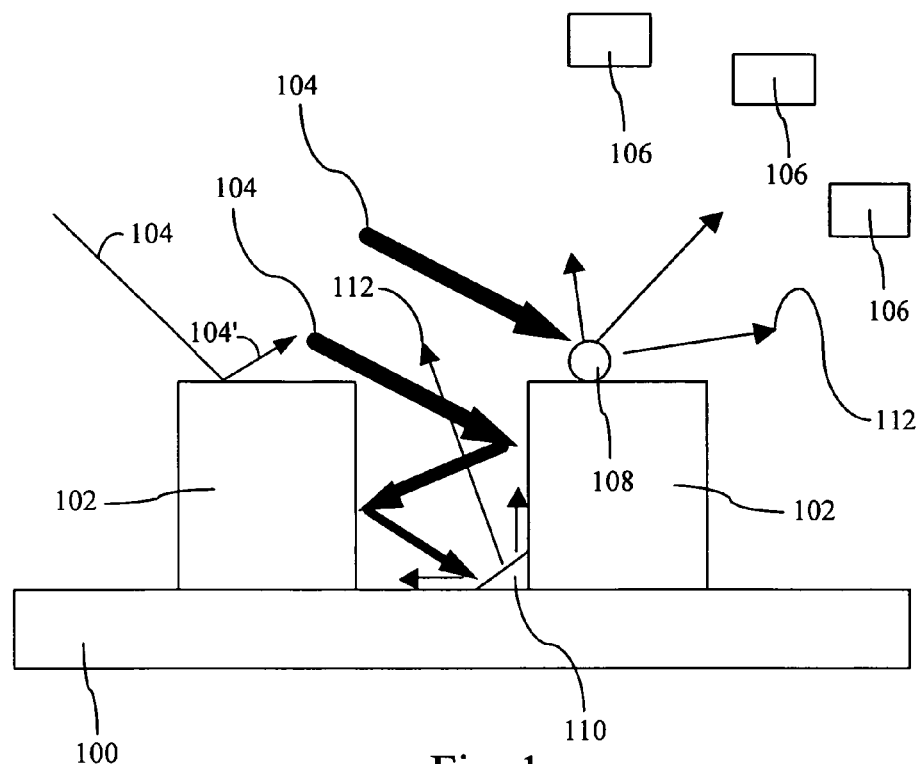
FIG. 1 is a schematic view showing the relative positions of a conventional defect detecting system, the incident light, the device pattern, and the defects.
Figure 2:
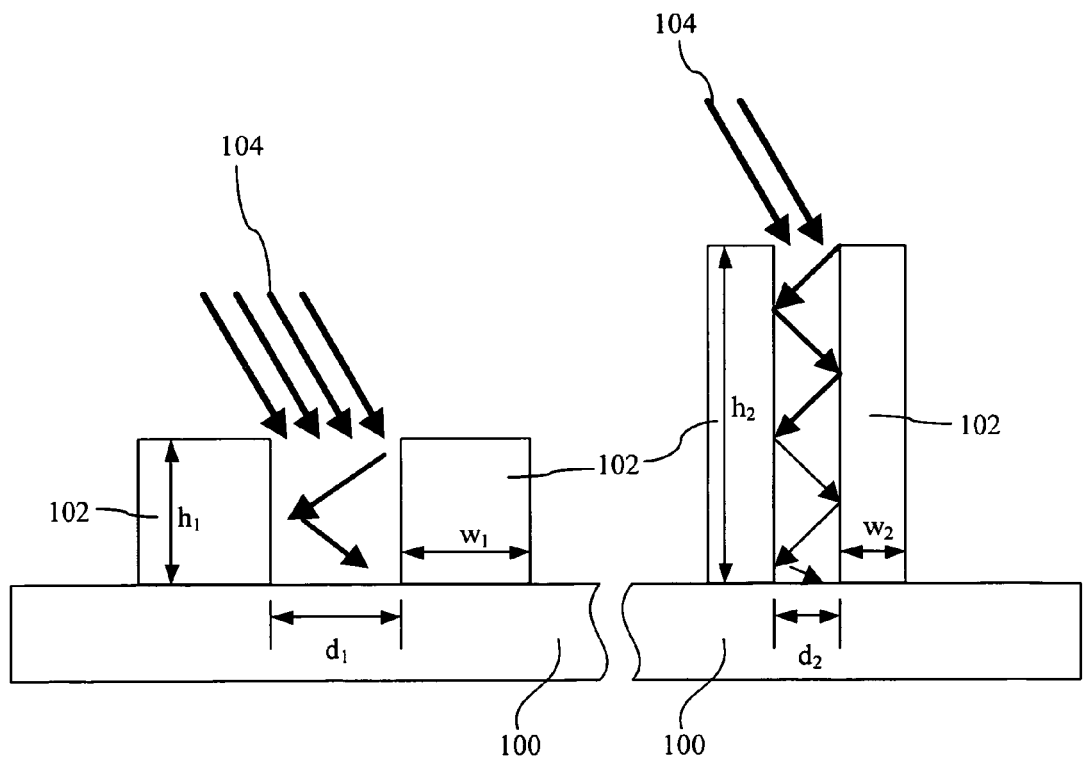
FIG. 2 is a schematic cross-sectional view of a sample showing the dimension of the device pattern.
Figure 3:
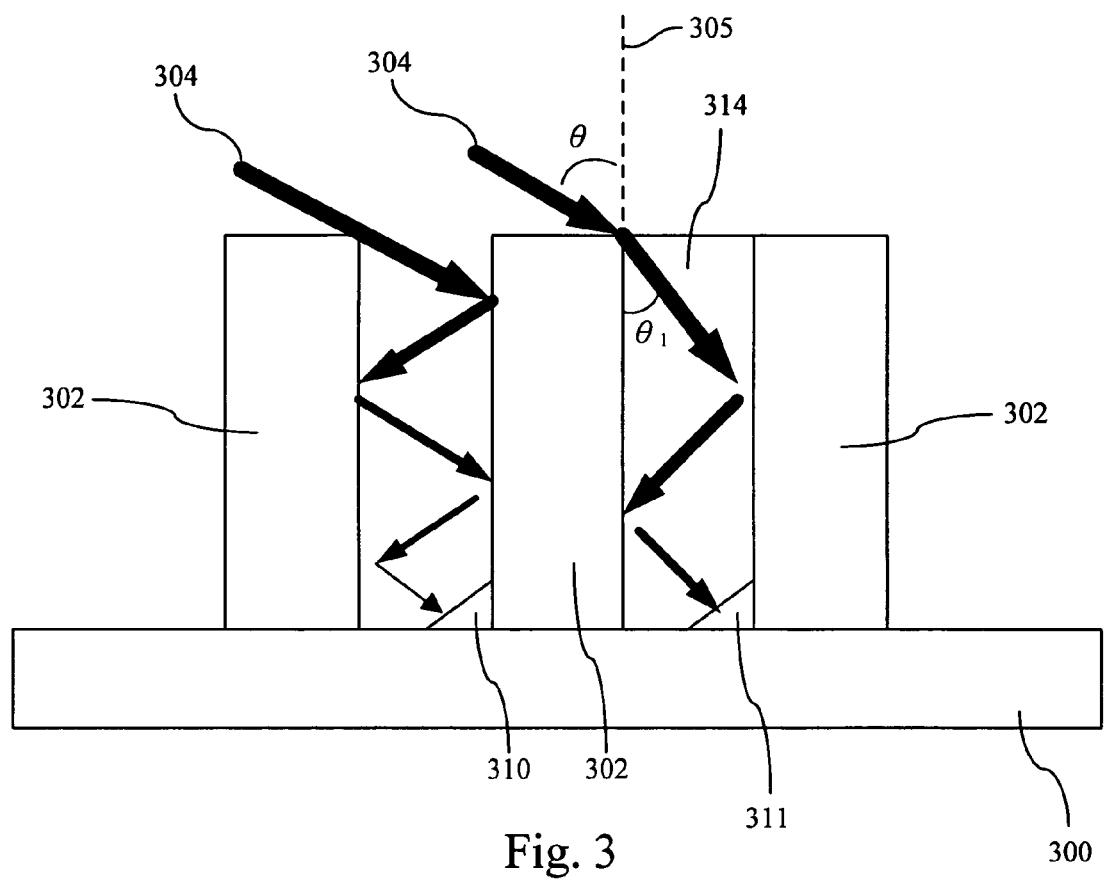
FIG. 3 is a schematic cross-sectional view of a sample illustrating the reflections of an incident light affected by the medium.

In the following, we describe the disclosed method with reference to the appropriate drawings. As shown in FIG. 3, the conventional defect detecting method is illustrated in the left plot. When an incident beam 304 enters from the surface of the device pattern 302 into the gap between two patterns 302 or a concave portion, the incident light 304 may experience several reflections before reaching the bottom defect 310 of the device pattern 302. The incident light 304 for detecting the defect loses its energy due to these reflections. Therefore, the intensity of the incident light on the bottom defect 301 is far weaker than that on the surface of the device pattern 302.

In accord with the invention, an appropriate medium is selected to cover the sample. The medium fills the gap between device patterns 302 or the concave portion, as shown in the right plot. The incident light 304 projected by the defect detecting system enters the medium in the gap from the surface of the device pattern 302. When the refractive index of the used medium is greater than that of the original medium (usually air) on the surface of the device pattern 302, the incident beam 304 with an incident angle θ changes its direction of propagation toward the normal 305, as indicated by the arrow. The incident light 304 then proceeds in the direction with an outgoing angle $\theta_1$. The change in its propagation direction enables the incident beam 304 to reach the defect 311 at the bottom of the device pattern 302 in fewer reflections. The intensity of the beam at the bottom defect is less attenuated. Therefore, the incident light projected at the defect 311 and the light scattered from it are stronger in intensity than from the defect 310. The sensitivity of the defect detecting system on the bottom defects of device patterns is thus enhanced. Please refer to FIG. 4. Suppose the incident beam can reach the bottom of the device pattern 402 with only one deflection, the outgoing angle $\theta_1$ is expressed as $[90-\tan^{-1}(h/d)]$. The range of the incident angle from the normal 416 is between 90° and $[90-\tan^{-1}(h/d)]$ degrees, that is $$90°>\theta_1>[90-\tan^{-1}(h/d)]°.$$

However, the angle between the incident beam and the horizontal line in a usual defect detecting system is normally greater than 30°. In other words, the incident angle is usually less than 60°. Therefore, the range of the incident angle $\theta_1$ is between 60° and $[90-\tan^{-1}(h/d)]$ degrees; i.e., $60°>\theta_1>[90-\tan^{-1}(h/d)]°$.

If the incident light cannot directly reach the bottom of the device pattern 402, then the number of reflections T experienced by the incident light can be expressed as:

$$T=h/(d\times\cot\theta_2) \qquad (1)$$

$$\text{Deflection angle } \theta_2=\cot^{-1}[h/(T\times d)] \qquad (2)$$

Table 1 shows the relation between the different generations of manufacturing processes and the number of reflections. It can be seen that when the incident angle of the detecting beam is 60° (i.e. when the angle between the incident beam and the horizontal line is 30°), the number of reflections of an incident beam increases as it proceeds in the device pattern. Thus, this inevitably increases the difficulty in detecting the bottom defects.

TABLE 1

|  | Generation of Processes | | | | |
| --- | --- | --- | --- | --- | --- |
|  | 0.2 μm | 0.17 μm | 0.14 μm | 0.12 μm | 0.11 μm |
| Ratio of device pattern height to pitch (h/d) | 1.48 | 1.74 | 3.54 | 4.13 | 4.5 |
| Number of reflections | 2.56 | 3.01 | 6.13 | 7.15 | 7.79 |

Figure 4:
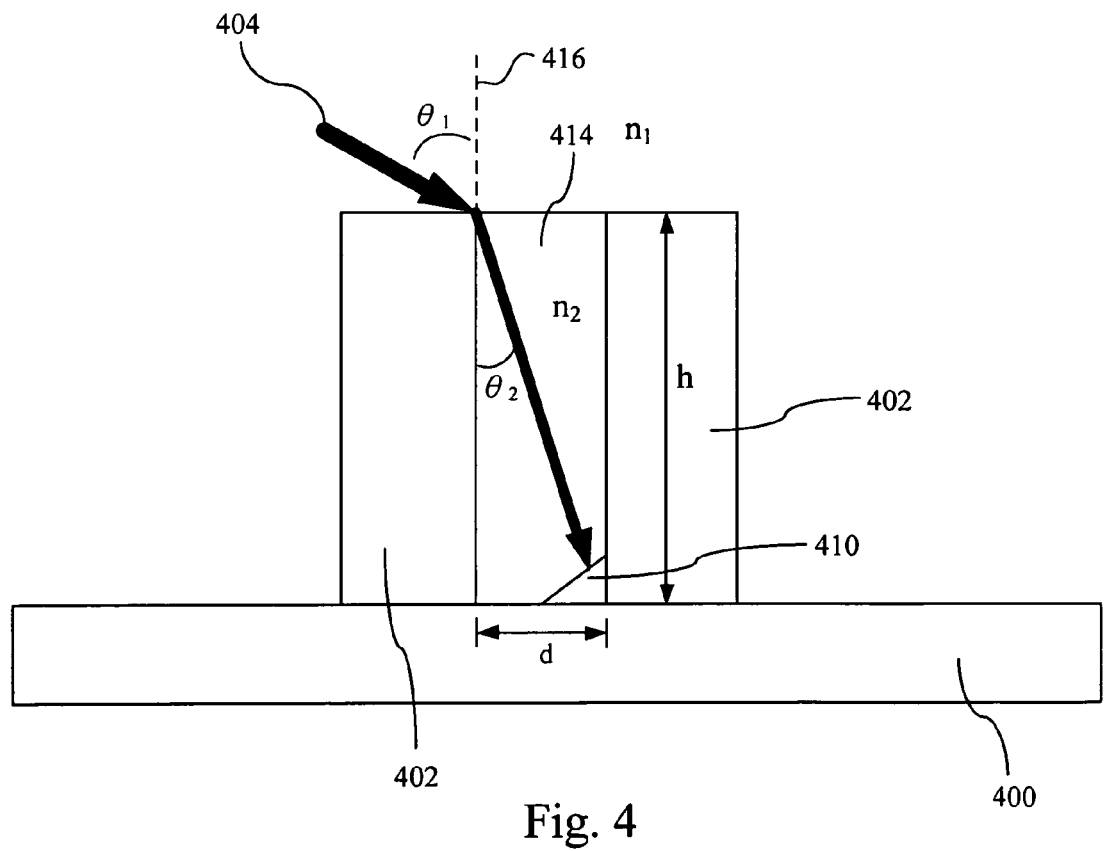
FIG. 4 is a schematic cross-sectional view showing the deflection after the incident enters the medium.

To solve the problem of increasing number of reflections for smaller device patterns, one can use the following formulas to determine a medium material with an appropriate refractive index to reduce the number of reflections during detection. As shown in FIG. 4, the angle between the incident beam 404 and the normal 416 is defined as the incident angle $\theta_1$. $\theta_2$ is defined as the deflection angle. $n_1$ is the refractive index of air above the surface of the device pattern 402. $n_2$ is the refractive index of the medium used in the invention. h is the height from the top surface of the device pattern 402 to the bottom. d is the pitch between adjacent device patterns 402. According to the Snell's Law, $$n_1 \times \sin\theta_1 = n_2 \times \sin\theta_2. \qquad (3)$$

With the help of Eq. (2), one can compute the refractive index of the medium on the sample as follows:

$$n_2 = n_1 \times \sin\theta_1 / \sin\{\cot^{-1}[h/(T \times d)]\}. \qquad (4)$$

The refractive index of air is about 1. Therefore, the refractive index of the medium is:

$$n_2 = \sin\theta_1 / \sin\{\cot^{-1}[h/(T \times d)]\}. \qquad (5)$$

Since the number of reflections $T \geq 1$, the refractive index of the medium on the sample can be expressed in another way as:

$$1 < n_2 < \sin\theta_1 / \sin\{\cot^{-1}[h/(d)]\}. \qquad (6)$$

Besides, the fewer reflections the incident light has, the less attenuation the incident light has. Take a device size of 0.12 μm as an example. If, with respect to the normal, the incident angle $\theta_1$ is 60° and the aspect ratio of the device h/d=4.13, the reflection occurs approximately 8 times; To enhance the sensitivity in detecting the bottom defects of the device pattern, the number of reflections has to be less than 8. For example, if the number of reflections of the incident light is expected to be between 3 and 4, then one should use a medium with a refractive index between 1.24 and 1.47.

Therefore, one can pick an appropriate medium according to the device aspect ratio (h/d) of the sample, the number of reflections an incident beam has (e.g., from 0 to 7), and the incident angle of the detecting beam from the selected defect detecting system. The sample can be a substrate with semiconductor device patterns formed on its surface. In particular, it is a semiconductor wafer having device patterns with a high aspect ratio. The medium covering the sample can be any material with a refractive index of $n_1 \times \sin\theta_1/\sin\{\cot^{-1}[h/(T \times d)]\}$ greater than 1, transparent to the incident beam, and not affecting the sample. Such materials include the dielectric materials (e.g. silicon oxide), photo resist, or a liquid that does not erode, oxidize, or dissolve the sample (e.g., deionized water and mineral oils) commonly used in semiconductor processes. The defect detecting system can be any conventional optical defect detecting system. The method of forming the medium on the sample can be coating, depositing, or any other approach.

Figure 5:
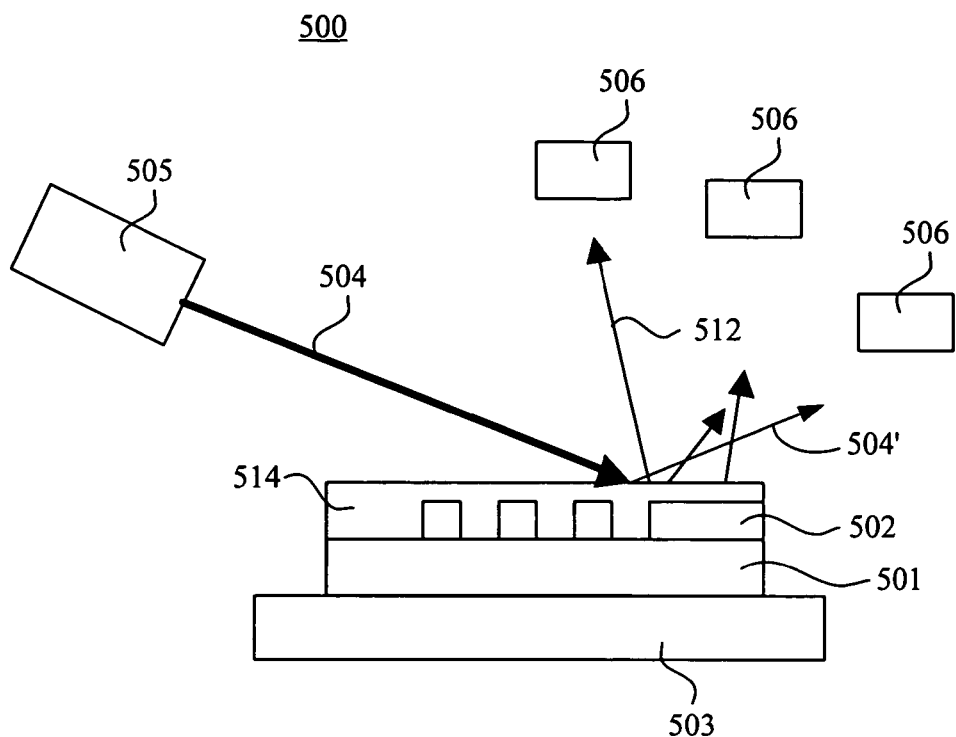
FIG. 5 shows a schematic view of the defect detection method according to a preferred embodiment of the invention.

In the following, we use a preferred embodiment to explain how the disclosed method is employed to detect defects on a semiconductor wafer. As shown in FIG. 5, a silicon dioxide is first coated on the wafer 501 as the medium 514 to reduce reflections. The silicon dioxide fills all gaps or concave portions in the device pattern 502. The wafer 501 coated with the medium 514 is then disposed on the sample stage 503 of the optical defect detecting system 500. The light source 505 in the system 500 projects the incident beam 504 on the surface of the wafer 501. The incident beam 504 penetrates through the medium 514 and reaches the bottom of the device pattern 502. The whole wafer 501 is scanned point by point. The incident light 504 is reflected and scattered by the surface and the bottom defect of the device pattern 502. The scattered light 512 and the reflected light 504' from the device pattern 502 are received by the detector 506 of the system 500. The intensity of the reflected and scattered light from all the device patterns 502 on the wafer 501 is obtained using the above method. The defect detecting system then compares the intensity from several consecutive device patterns on the wafer 501 to determine the defect distribution in these device patterns 502.

Figure 6:
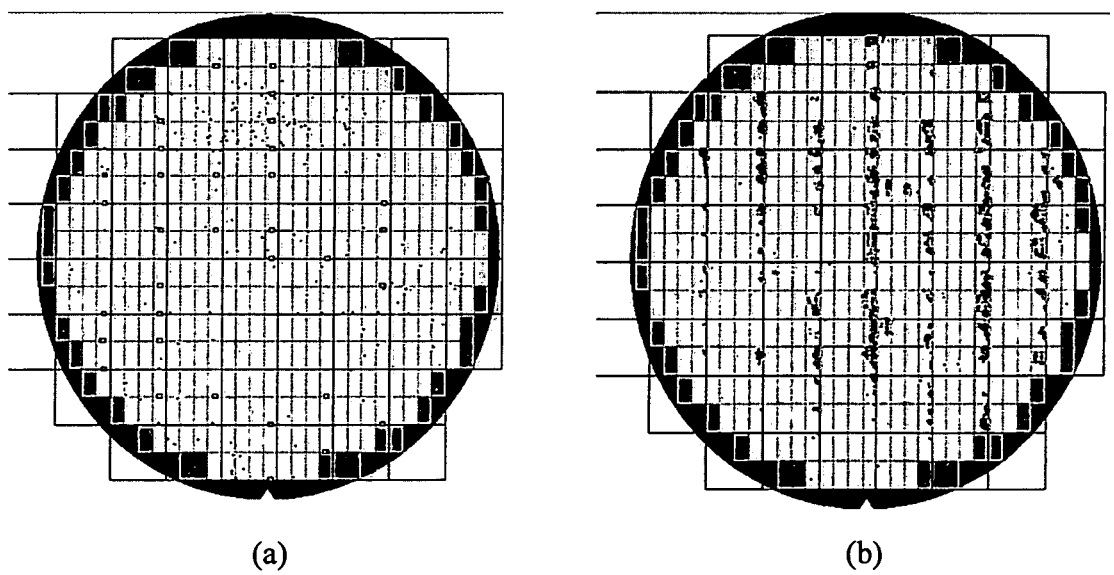
FIG. 6 shows the defect detection results using the conventional method and the disclosed method.

FIG. 6 shows the detection result of the sample wafer 501. FIG. 6(a) shows the defects detected using the conventional method. FIG. 6(b) shows the defected detected using the disclosed method. In FIG. 6, each black spot on the wafer is a defect. It is clear that the disclosed method can find out small defects on the device patterns with a higher sensitivity.

It is seen from the preferred embodiment that the invention has the following advantages. First, the invention can avoid or reduce the problem of attenuating energy due to repeated reflections of the incident light in the gap of device patterns.

Another advantage of the invention is that the ability of detecting the bottom defects in device patterns can be enhanced without affecting the signal from the surface defects of the device pattern.

A further advantage of the invention is to avoid complicated modifications to the existing defect detecting system.

Yet another advantage of the invention is to solve the problem that it is difficult for a conventional defect detecting system to detect bottom defects in device patterns as the size of the device patterns gets smaller.

While the invention has been described by way of example and in terms of the preferred embodiment, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method for improving the sensitivity of defect detection, comprising the steps of:
    providing a substrate having a plurality of device patterns;
    covering a medium on the substrate and between the device patterns, wherein the medium has a refractive index greater than 1;
    projecting a beam of light on the substrate for the light to penetrate through the medium and reach the bottom of the device patterns;
    using a plurality of detectors to receive reflected light from the surface of the substrate and scattered light from the bottom of the device patterns; and
    analyzing the intensities of the reflected and scattered light from each point of at least two consecutive device patterns, wherein a point with variations of intensities is identified as a defect distribution on the device patterns,
    wherein a ratio of height to pitch of the device patterns is greater than 3.

2. A method for improving the sensitivity of defect detection, comprising the steps of:
    providing a substrate having a plurality of device patterns;
    covering a medium on the substrate and between the device patterns, wherein the medium has a refractive index greater than 1;
    projecting a beam of light on the substrate for the light to penetrate through the medium and reach the bottom of the device patterns;
    using a plurality of detectors to receive reflected light from the surface of the substrate and scattered light from the bottom of the device patterns; and
    analyzing the intensities of the reflected and scattered light from each point of at least two consecutive device patterns, wherein a point with variations of intensities is identified as a defect distribution on the device patterns, wherein the refractive index of the medium is $\sin\theta/\sin\{\cot^{-1}[h/(T\times d)]\}$ where $\theta$ is the incident angle of the incident beam, h is the height of the device patterns, d is the pitch between the device patterns, and T is the number of reflections of the incident beam in the device patterns.

3. The method of claim 2, wherein the refractive index of the medium is smaller than $\sin\theta/\sin[\cot^{-1}(h/d)]$.

4. A method for improving the sensitivity of defect detection, comprising the steps of:
  covering a medium on a substrate having a plurality of device patterns, wherein the refractive index of the medium is greater than 1 and smaller than $\sin\theta/\sin[\cot^{-1}(h/d)]$ where $\theta$ is the incident angle of an incident beam, h is the height of the device patterns, and d is the pitch between the device patterns, wherein a ratio of the height to the pitch of the device patterns is greater than 3;
  projecting a beam of light on the substrate for the light to penetrate through the medium and reach the bottom of the device patterns;
  using at least a detector to receive reflected light from the surface of the substrate and scattered light from the bottom of the device patterns; and
  comparing the intensities of the reflected light and the scattered light from each point of at least two consecutive device patterns, wherein a point with variations of intensities is identified as a defect distribution on the device pattern.

5. The method of claim 4, wherein an angle between the incident light and the normal of the substrate is between 90° and $[90-\tan^{-1}(h/d)]°$.

6. The method of claim 4, wherein an angle between the incident light and the normal of the substrate is between 60° and $[90-\tan^{-1}(h/d)]°$.

7. The method of claim 4, wherein the medium comprises silicon oxide.

8. The method of claim 4, wherein the medium comprises a photo-resist.

9. The method of claim 4, wherein the medium is selected from a group consisting of water and a mineral oil.

10. The method of claim 4, wherein the substrate is a semiconductor wafer.

* * * * *